(12) United States Patent
Sheppard et al.

(10) Patent No.: US 9,384,567 B2
(45) Date of Patent: Jul. 5, 2016

(54) COMPUTED TOMOGRAPHY IMAGING PROCESS AND SYSTEM

(71) Applicant: FEI Company, BS Eindhoven (NL)

(72) Inventors: Adrian Paul Sheppard, Fisher (AU); Andrew Maurice Kingston, Holder (AU); Trond Karsten Varslot, Vuku (NO)

(73) Assignee: FEI Company, Hillsboro, OR (US)

( * ) Notice: Subject to any disclaimer, the term of this patent is extended or adjusted under 35 U.S.C. 154(b) by 124 days.

(21) Appl. No.: 14/349,429

(22) PCT Filed: Oct. 3, 2012

(86) PCT No.: PCT/AU2012/001204
§ 371 (c)(1),
(2) Date: Apr. 3, 2014

(87) PCT Pub. No.: WO2013/049888
PCT Pub. Date: Apr. 11, 2013

(65) Prior Publication Data
US 2014/0233691 A1    Aug. 21, 2014

(30) Foreign Application Priority Data
Oct. 3, 2011 (AU) ................................ 2011904072

(51) Int. Cl.
*A61B 6/00* (2006.01)
*G06T 11/00* (2006.01)
*G01N 23/04* (2006.01)

(52) U.S. Cl.
CPC ............ *G06T 11/005* (2013.01); *G01N 23/046* (2013.01); *G01N 2223/419* (2013.01); *G01N 2223/616* (2013.01)

(58) Field of Classification Search
CPC ................ A61B 6/032; G01N 23/046; G01N 2223/419; G01N 2223/616; G01N 23/04; G06T 11/005; G06T 2207/10081

USPC ................ 378/4–20; 382/128–132
See application file for complete search history.

(56) References Cited

U.S. PATENT DOCUMENTS

| | | | |
|---|---|---|---|
| 8,938,111 B2 * | 1/2015 | Kingston ............... | A61B 6/032 128/922 |
| 2004/0081270 A1 * | 4/2004 | Heuscher ............... | A61B 6/032 378/4 |
| 2007/0019776 A1 * | 1/2007 | Bontus ................... | A61B 6/032 378/4 |

FOREIGN PATENT DOCUMENTS

| | | |
|---|---|---|
| CN | 100 401 983 C | 7/2008 |
| EP | 0 662 305 A1 | 7/1995 |

OTHER PUBLICATIONS

International Search Report, International Application No. PCT/AU2012/001204, Dated: Nov. 12, 2012.
European Search Report for corresponding EP Application No. 12 838 639.8.

* cited by examiner

*Primary Examiner* — Courtney Thomas
(74) *Attorney, Agent, or Firm* — Hamilton, Brook, Smith & Reynolds, P.C.

(57) ABSTRACT

A computed tomography imaging process, including: acquiring projection images of an object by detecting radiation that has passed through the object for respective different relative orientations of the object and the radiation; and processing the projection images to generate a tomogram of the object; wherein the radiation passes through the object in the form of a diverging beam, and the different relative orientations of the object and the beam of radiation define two or more complete trajectories of the beam along the object, the complete trajectories being mutually offset to reduce the degradation of spatial resolution in portions of the generated tomogram due to the divergence of the beam through the object.

22 Claims, 11 Drawing Sheets

COMPUTED TOMOGRAPHY IMAGING PROCESS AND SYSTEM

This application is the U.S. National Stage of International Application No. PCT/AU2012/001204, filed Oct. 3, 2012, which designates the U.S., published in English, and claims priority under 35 U.S.C. §§119 or 365(c) to Australian Application No. 2011904072, filed Oct. 3, 2011.

TECHNICAL FIELD

The present invention relates to a computed tomography imaging process and system.

BACKGROUND

The term computed tomography (CT) usually refers to processes whereby one or more images representing essentially any desired view of the internal structures of a physical object of interest are computed from a corresponding set of images representing respective geometric projections of the object.

To acquire the projection images of an object, a tomographic imaging apparatus requires: (i) a source of particles or electromagnetic radiation to probe the object, (ii) a detector to measure the resultant probe-object interactions, and (iii) a means for changing the relative orientation between the source/detector components and the object. The projection images constituting the image set thus represent measurements of the probe-object interactions acquired at respective relative orientations between the source/detector components and the object. These directions are typically chosen such that the source and detector follow a particular trajectory relative to the object, the trajectory depending on the geometry between the source and the detector. Examples of such trajectories include circular, helical and saddle trajectories.

Once the set of two-dimensional projection images at respective different relative orientations has been acquired, reconstruction algorithms are applied to these images to generate a corresponding data set referred to herein as a tomogram, representing the external and internal features of the object in three spatial dimensions. Using the tomogram as input, display software can then be used to visualise the object in essentially any way desired by a user, including as a rotating semi-transparent object, static and dynamic slices through the object along arbitrary directions, and the like. Such 'reconstructed' images are referred to herein as tomographic images.

X-ray computed-tomography (CT) enables non-destructive inspection of complex internal structures for a wide range of materials and length scales. It is a rapidly evolving technology which is readily finding new applications in fields such as biology, geology and materials science. CT systems capable of producing CT images of micron-scale features are referred to in the art as micro-CT systems. Current state-of-the-art lab-based micro-CT systems typically spend 8-12 hours acquiring x-ray projection data of a sample or object of interest in order to produce a high-quality tomogram containing $2048^3$ voxels, with voxel side-lengths of 2-3 microns.

However, in many applications, the features of interest are too small to be clearly resolved in micro-CT images with this spatial resolution. For example, FIG. 1 compares a micro-CT image slice (left-hand image) from a tomogram with a 2.5 μm voxel (edge) size with a scanning electron microscope (SEM) image (right-hand image) with a 0.7 μm pixel dimension of the same region. The open regions of the sample visible in the SEM image are not clearly resolved in the micro-CT image, precluding use of the latter for accurate quantitative analysis of the sample porosity. As discussed below, the spatial resolution of micro-CT can be improved at the expense of significantly longer acquisition times. However, longer acquisition times increase the per-image cost and decrease throughput, which are generally undesirable for micro-CT systems in commercial environments.

Achieving increased resolution while maintaining acceptable acquisition times is a major challenge for lab-based cone-beam micro-CT systems. For resolutions at or below the micron scale, existing CT systems and methods require prolonged acquisition times to keep the signal-to-noise ratio (SNR) from compromising image fidelity. However, reduced acquisition times would improve specimen throughput, thereby increasing the appeal of micro-CT imaging in a range of commercial applications.

High-Resolution Imaging and Signal-to-Noise Ratio

A major obstacle when increasing the image resolution of lab-based cone-beam micro-CT systems is the relationship between radiographic resolution, X-ray source spot size, and projection data signal-to-noise ratio (SNR). Due to penumbra effects, the lower limit to radiographic resolution is the X-ray source spot diameter; however, X-ray flux is roughly proportional to source spot area. Therefore, in order to increase the resolution by a factor of 2, one must decrease the source spot area, and consequently the X-ray flux, by a factor of 4. The dominant contribution to image noise in a properly configured (i.e., quantum limited) detector is shot noise (i.e., statistical noise) arising from finite photon numbers. The projection data SNR scales with the square root of the number of X-ray photons detected at each pixel of the detector. Consequently, to maintain a given SNR and double the resolution, the acquisition time must be 4 times longer. At high resolutions, this square-law relationship leads to unacceptably long acquisition times, and high resolution imaging also places stringent stability requirements on system components.

X-ray tubes generally produce a near-isotropic x-ray beam flux over a solid angle of almost $2\pi$ steradians. The simplest way to alleviate the diminishing SNR is to move the detector closer to the source, thereby capturing a larger proportion of the X-ray beam.

However, this means operating the imaging system at a high cone-angle, as will be apparent from the system geometry shown in FIG. 2.

Data Sufficiency

As described above, tomograms and tomographic images are not acquired directly, but are reconstructed from a set of acquired projection images of the specimen. The X-ray source and detector (or equivalently: the sample) move along a predetermined trajectory, so that each projection image is collected at a different projection angle. The algorithm used to reconstruct a tomogram depends largely on the trajectory used for collecting the projections.

In order to reconstruct an accurate tomogram or tomographic image, the acquired projection data should contain complete information about the object. Data completeness for 3D tomography was first addressed by Tuy (see H. K. Tuy, "An inverse formula for cone-beam reconstruction," *SIAM J Appl. Math*, vol. 43, pp. 546-552, 1983). Tuy formulated a general criterion for acquisition trajectories which guarantees that complete information can be collected. A trajectory that satisfies this criterion is referred to in the art as a complete trajectory. However, it will be understood by those skilled in the art that the completeness of a trajectory is dependent upon the tomographic volume that is reconstructed. Consequently, in this specification the term complete trajectory is defined as one that satisfies the Tuy criterion for at least a substantial fraction of the reconstructed tomogram.

A single closed circle trajectory does not provide complete data for 3D reconstruction. Regardless of sampling density, data collected along such a trajectory does not contain all the information needed to reconstruct the object, and consequently only an approximate reconstruction is possible. As long as the cone-angle is small, acquiring projection data along a circle trajectory is almost complete (e.g., a cone-angle of <5° is typically acceptable). However, the amount of missing data increases as the cone-angle increases.

A complete trajectory can be obtained by appending to the circle a line segment perpendicular to the circle plane. Other such complete trajectories include a helix, and a saddle. Projection data collected along these (and other complete) trajectories provide sufficient information for (theoretically) exact reconstruction. Indeed, theoretically-exact reconstruction algorithms have been known for some time. Although exact reconstruction is not achieved in practice due to factors such as noise and finite sampling, it is nevertheless desirable to use theoretically-exact reconstruction methods in order to remove systematic errors in the reconstruction due to approximations in the underlying inversion formula.

Using a complete trajectory, in principle a tomographic imaging apparatus can operate at an arbitrarily large cone-angle, opening up the possibility of moving the detector as close to the source as physically possible. With the added benefit of being able to image objects of arbitrary height, the helix is of particular interest. A number of known reconstruction methods are able to generate tomograms from projection data acquired along a helical trajectory, including approximate iterative methods such as the Algebraic Reconstruction Technique (ART) and the Simultaneous Iterative Reconstruction Technique (SIRT), and filtered backprojection-type reconstruction methods based on the theoretically-exact Katsevich 1PI inversion formula, or helix variants of the approximate Feldkamp-Davis-Kress (FDK) reconstruction method.

Several existing types of CT systems can achieve (sub) micrometer resolution. For example, ultra-fine-focus systems utilise scanning electron microscopes (SEM) for X-ray generation. However, these can only produce X-rays up to about 30 kV, and are limited to sub-millimeter specimen diameter. Furthermore, since the specimen is placed in a vacuum chamber, they cannot easily accommodate experimental rigs.

X-ray lens based systems use a condenser lens to increase X-ray flux from the source. These systems are also limited to low X-ray energies due to the high aspect ratios required in the Fresnel zone plates for hard X-rays. Good resolution is obtained by using very small detector elements, mandating a very thin scintillator. As a result, only a small fraction of the X-ray photons are detected, leading to long acquisition times despite the relatively high X-ray flux in these systems.

Fine focus systems are a third alternative. Like ultra-fine-focus systems, they do not rely on X-ray optics, but offer much greater flexibility both in the range of X-ray energies which can be used—and as a consequence what objects can be imaged—since no vacuum chamber is needed. Furthermore, the propagation path between the X-ray source and the detector is completely open, making such systems ideally suited when auxiliary experimental rigs are required.

A fourth configuration type is the quasi parallel configuration, in which the sample is placed closer to the detector than the source, giving a geometric magnification close to 1. This geometry enables a much higher radiographic resolution for a given source spot size than the fine focus configuration, allowing the use of sources with a much higher flux. However, the larger source-sample distance mandates the use of a smaller cone angle, meaning that in practice the x-ray flux incident on the sample is not improved dramatically. Secondly, at high resolution a thin scintillator must be used, resulting in a very low X-ray detection efficiency, typically less than 5%, compared to over 60% for modern large flat-panel detectors.

The following discussion deals exclusively with the fine-focus system type.

Conventional fine-focus micro-CT systems are lens-free fine-focus configurations that use a circular trajectory, and reconstruction is performed with the Feldkamp-Davis-Kress (FDK) algorithm. This offers great simplicity and reliability, as it requires only a single rotation stage. As described above, however, collecting projection data along a circular trajectory does not provide complete information about the object, and is not suited for imaging with x-ray beam cone-angles beyond 5°. Consequently, to obtain an acceptable SNR, long acquisition times are used. These same limitations apply to circular trajectory ultrafine-focus systems which utilise scanning electron microscopes (SEM) for X-ray generation.

The commercial helical micro-CT system manufactured by SkyScan uses a fine-focus helical trajectory and FDK reconstruction. As described above, the helical trajectory is complete. However, the approximate nature of the FDK reconstruction algorithm means that data acquisition can only be performed with a moderate or small helix pitch, necessitating long acquisition times when scanning a long object.

In principle, reconstruction methods based on exact inversion formulas can be used to perform tomographic imaging at arbitrarily high cone-angle, and are therefore not limited to a small pitch. However, the inventors have identified that, at high pitch, the inherent asymmetry of the helix trajectory implies that the acquired set of projections represents an uneven spatial sampling of the imaged object. This leads to tomograms with substantially non-uniform spatial resolution, and therefore reduced utility.

It is desired to provide a computed tomography imaging process and system that alleviate one or more difficulties of the prior art, or that at least provide a useful alternative.

SUMMARY

In accordance with some embodiments of the present invention, there is provided a computed tomography imaging process, including:
  acquiring projection images of an object by detecting radiation that has passed through the object for respective different relative orientations of the object and the radiation; and
  processing the projection images to generate a tomogram of the object;
  wherein the radiation passes through the object in the form of a diverging beam, and the different relative orientations of the object and the beam of radiation define two or more complete trajectories of the beam along the object, the complete trajectories being mutually offset to reduce the degradation of spatial resolution in portions of the generated tomogram due to the divergence of the beam through the object.

The processing can also reduce the variation in spatial resolution in the tomogram.

In some embodiments, the different relative orientations of the object and the beam of radiation define a single trajectory that defines the two or more complete trajectories. That is, the single trajectory includes the two or more complete trajectories. In other embodiments, the two or more complete trajectories are acquired independently.

In some embodiments, the two or more complete trajectories are helical trajectories. In some embodiments, the two or more complete trajectories include two helical complete trajectories mutually offset by 180°.

In some embodiments, the processing of the projection images includes:

processing the projection images for each of the two or more complete trajectories to generate a corresponding first tomogram, wherein the spatial resolution of each said first tomogram varies with spatial location within the object in accordance with the corresponding complete trajectory; and processing the first tomograms to generate a further tomogram in which the variation in spatial resolution is at least partially compensated.

In some embodiments, the further tomogram is generated by combining selected portions of the first tomograms.

In some embodiments, the further tomogram is generated as a weighted combination of the first tomograms. In some embodiments, the weights are equal. In other embodiments, the weights are determined so that each portion of the further tomogram corresponds to the sharpest of the corresponding portions of the first tomograms.

Some embodiments of the present invention provide a computed tomography imaging process, including:

accessing sets of projection images of an object or tomograms generated from the sets of projection images of an object, each said set of projection images having been acquired using a corresponding complete trajectory of a beam of radiation relative to the object, wherein the beam divergence through the object degrades the spatial resolution in parts of the corresponding tomogram or in parts of a tomogram generated from the corresponding set of projection images, were such a tomogram to be generated, in accordance with the corresponding complete trajectory; and generating a further tomogram from the tomograms or sets of projection images to reduce the degradation in spatial resolution.

Some embodiments of the present invention provide a computed tomography imaging process, including:

accessing sets of projection images of an object acquired using respective different complete trajectories of a beam of radiation relative to the object, wherein the beam divergence through the object would degrade the spatial resolution in portions of respective tomograms generated from the respective Sets of projection images, were such tomograms to be generated, in accordance with the respective complete trajectories; and processing the sets of projection images to generate a tomogram in which the degradation in spatial resolution is reduced.

In some embodiments, the tomogram is generated from the projection images using an exact or approximate filtered backprojection-type method. In other embodiments, the tomogram is generated from the projection images using an iterative approximate method.

The present invention also provides a computer-readable storage medium having stored thereon computer-executable programming instructions configured for execution of any one of the above processes.

Some embodiments of the present invention provide a computer-readable storage medium having stored thereon a computer program product configured for execution of any one of the above processes.

Some embodiments of the present invention provide a computed tomography imaging system configured to execute any one of the above processes.

In accordance with some embodiments of the present invention, there is provided a computed tomography imaging system, including:

a data acquisition module configured to acquire projection images of an object generated by detecting, radiation that has passed through the object for respective different relative orientations of the object and the radiation; and a tomogram generator configured to process the projection images to generate a tomogram of the object;

wherein the radiation passes through the object in the form of a diverging beam, and the different relative orientations of the object and the beam of radiation define two or more complete trajectories of the beam along the object, the complete trajectories being mutually offset to reduce the degradation of spatial resolution in portions of the generated tomogram due to the divergence of the beam through the object.

In some embodiments, the tomogram generator is configured to process the projection images for each of the complete trajectories to generate a corresponding first tomogram, wherein the spatial resolution of each said first tomogram varies with spatial location within the object in accordance with the corresponding complete trajectory; and to process the first tomograms to generate a further tomogram in which the variation in spatial resolution is reduced or at least partially compensated.

BRIEF DESCRIPTION OF THE DRAWINGS

Some embodiments of the present invention are hereinafter described, by way of example only, with reference to the accompanying drawings, wherein like reference numbers refer to like elements, and wherein.

DETAILED DESCRIPTION

Some embodiments of the present invention are described below in the context of a tomographic imaging apparatus for micrometer-scale or nanometer-scale computed tomography of small objects, such as cylindrical geological core samples, using a cone-shaped x-ray beam. However, it should be understood that the processes described herein are generally applicable to a wide range of different tomographic methods and apparatus, and are not in general limited to any particular apparatus type, radiation type (including particles), object type, or length scale.

Figure 1:
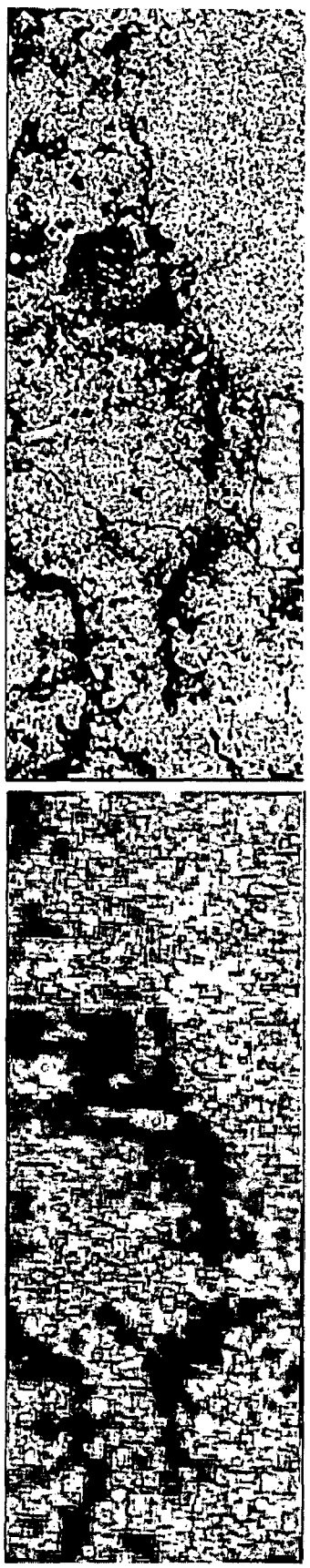
FIG. 1 includes a conventional micro-CT image (left-hand image) and an SEM image (right-hand image) of the same region of a geological core sample, demonstrating the relatively poor spatial resolution of conventional micro-CT that prevents quantitative analysis of sample porosity.
Figure 2:
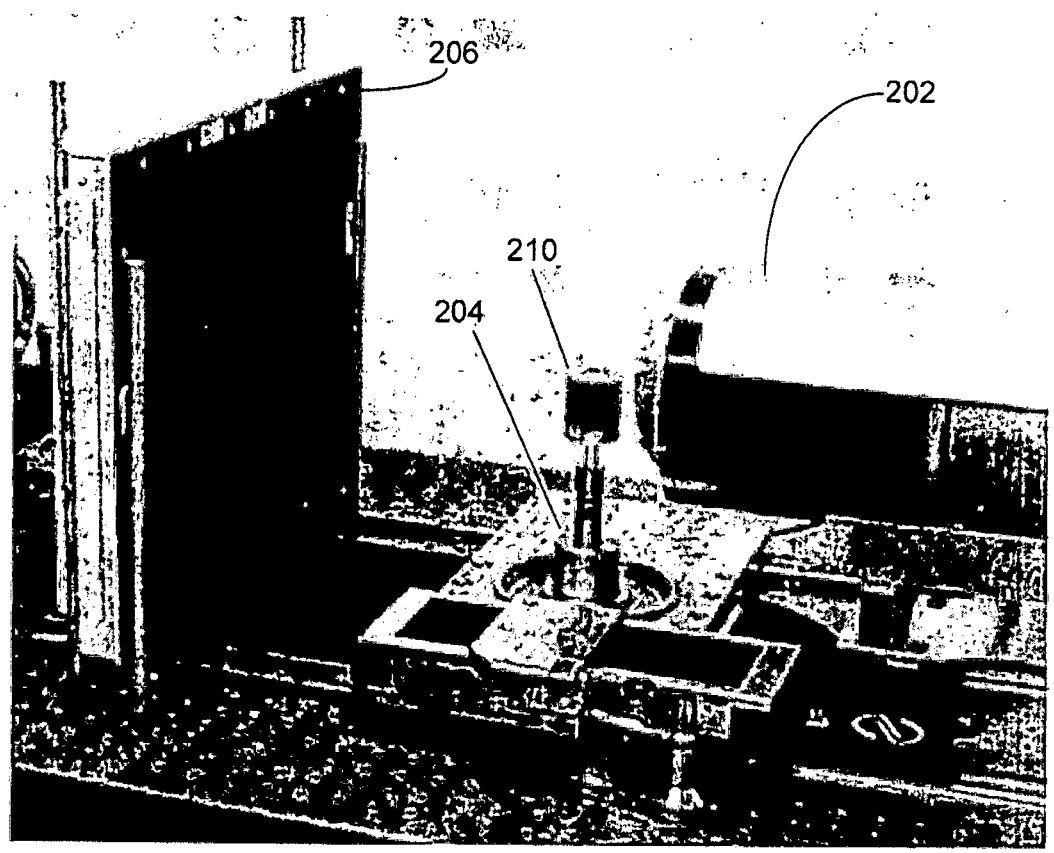
FIG. 2 is a photographic image of a tomographic imaging apparatus in which a cone-shaped x-ray beam generated by an x-ray source is transmitted through an object or sample of interest to produce projection images on a detector.
Figure 3:
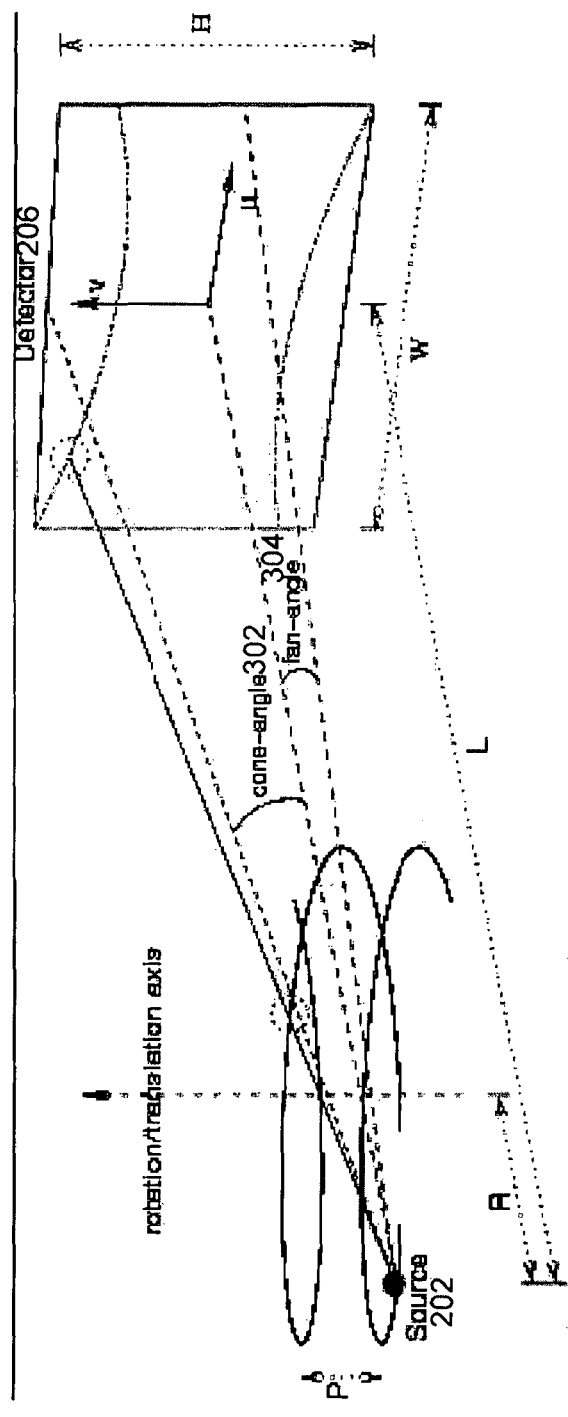
FIG. 3 is a schematic diagram illustrating geometric parameters of a tomographic imaging apparatus such as the one shown in FIG. 2 where a helical complete trajectory is used.

As shown in FIGS. 2 and 3, a computed tomography (CT) apparatus or system includes an x-ray source 202, a sample stage 204, and a detector 206. The x-ray source 202 generates a cone-shaped x-ray beam that is transmitted through an object 210 mounted on the sample stage 204 to the detector 206. The cone angle 302 and the fan angle 304 are defined, respectively, as the vertical and horizontal half-angles subtended by the detector 206 at the source 202. The detector 206 includes a scintillator that generates visible light when irradiated by x-rays, and a CCD or amorphous silicon flat panel sensor mounted behind the scintillator that generates image data representing two-dimensional images of the spatial arrangement of scintillations generated by the scintillator, thus producing a two-dimensional image or map of x-ray intensity for the x-rays transmitted through the object 210. As will be appreciated, each of these images shows both external and internal structural features of the object 210, as projected along the directions of x-rays transmitted through the object 210 to the detector 206. The image data generated by the detector 206 is acquired as a set of images 1536 stored in the form of binary data in a computer system 1500 of the system for subsequent processing, as shown in FIG. 15. The images are acquired sequentially, with the sample stage 204 being actuated to rotate the sample or object 210 by a small angle (and, in the case of helical scanning, to also translate the sample or object 210 by a small vertical distance) between successive images, thus providing different geometric projections through the object 210. These steps are repeated until the sample has undergone a rotation of at least 180°+fan angle and a complete set of projection images has been acquired. In the case of helical scanning, the steps are repeated until the sample or object 210 has undergone sufficient linear translation and rotation that complete information has been obtained for the regions of interest of the sample/object 210. The path represented by the collective stepwise relative movements of the x-ray beam and the object 210 is referred to in the art as the 'scan trajectory' (or, for convenience, simply the 'trajectory'), with the projection images 1536 being acquired at respective positions along this trajectory.

The set of projection images 1536 is then processed using reconstruction software to generate a tomogram representing the three-dimensional external and internal structural features of the object 210. To this end, various reconstruction methods are available, both approximate iterative methods such as ART and SIRT, and filtered backprojection-type methods. In the described embodiments, an optimisation-based reconstruction method for helix trajectories is used where the Katsevich 1PI inversion formula (as described in A. Katsevich, "Theoretically exact filtered backprojection-type inversion algorithm for spiral CT," *SIAM Journal of Applied Math*, pp. 2012-2026, 2002) is combined with an auto-alignment process, as described in International Patent Application No. PCT/AU2011/000038, the entirety of which is hereby expressly incorporated herein by reference. The resulting tomogram can be displayed in the form of a partially transparent representation of the object 210 that can be dynamically rotated and sliced in real-time by a user of the system to visualise and analyse the internal structural features of the object 210.

Figure 4:
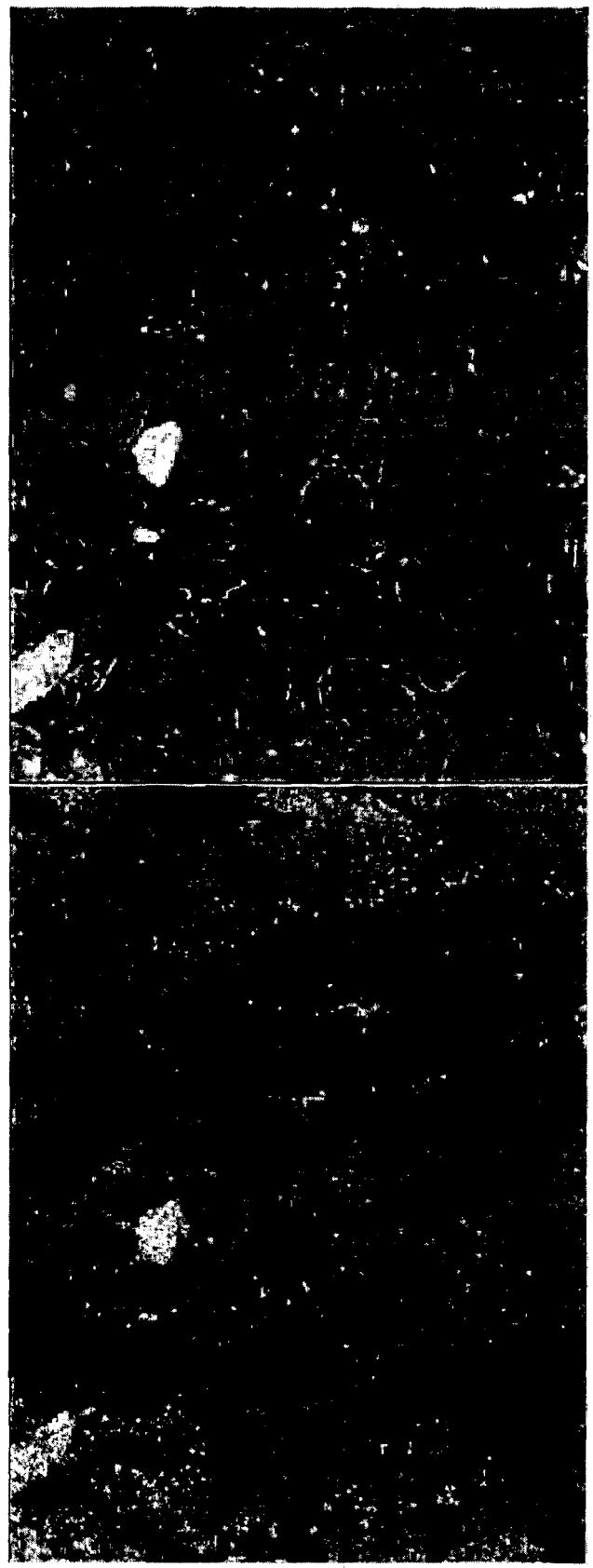
FIG. 4 includes images of reconstructed tomogram slices showing the same portion of a geological core sample for a circular trajectory (left-hand image) and a helical trajectory (right-hand image)

The CT apparatus or system shown in FIG. 2 is a high-precision micro-CT instrument capable of acquiring X-ray projection data using a wide range of object trajectories. For example, FIG. 4 contrasts a cross-section of a tomogram generated by this system using a helical trajectory (right-hand image) with a tomogram cross-section generated from data acquired on a traditional micro-CT system using a circular trajectory (left-hand image), the latter requiring a significantly longer camera-length in order to image the same tomographic volume. The spatial resolution of the helical trajectory tomogram cross-section (right-hand image) is clearly superior to that of the circular trajectory tomogram (left-hand image).

Figure 5:
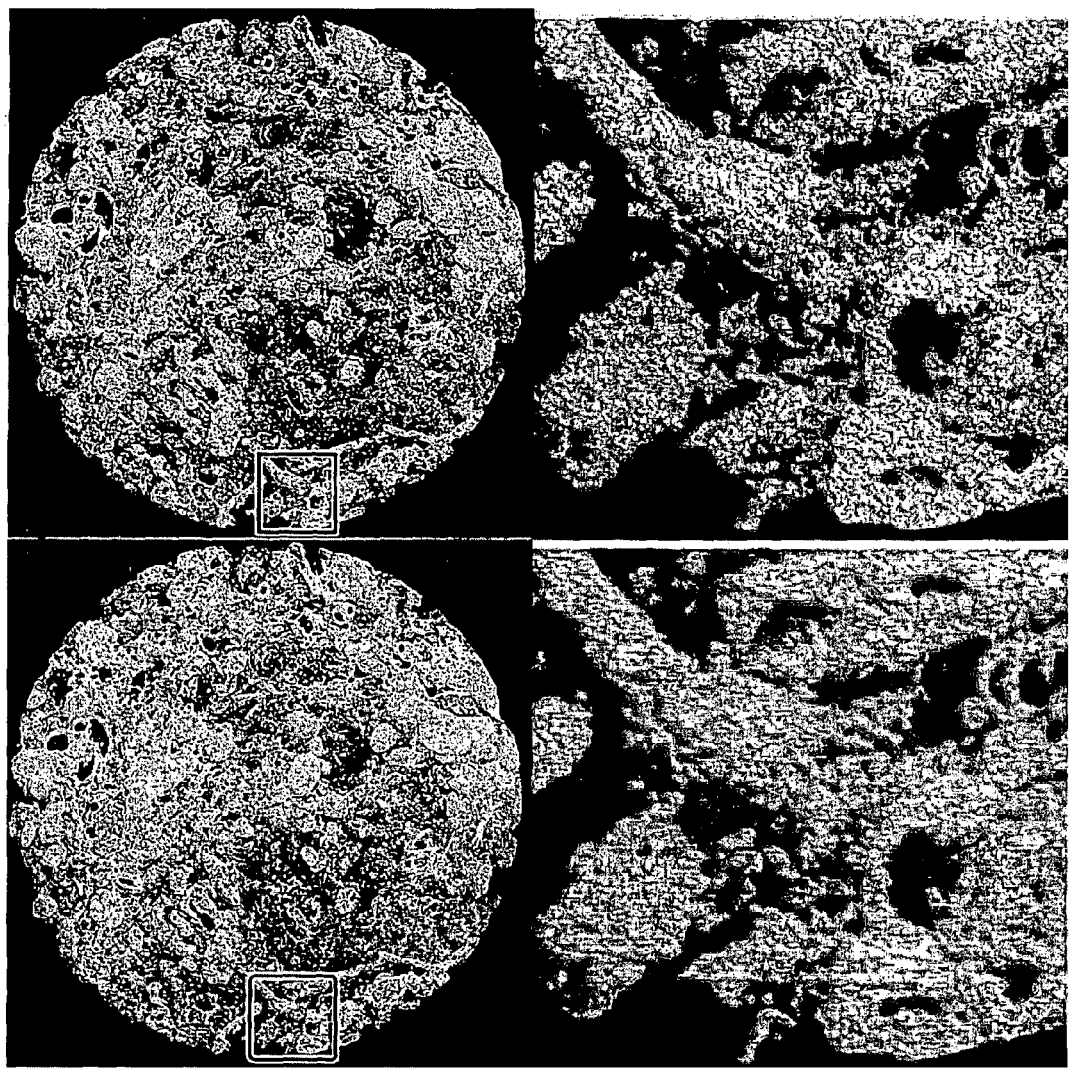
FIG. 5 includes (left-hand) images of corresponding tomogram cross-sections of a geological core sample for helical complete trajectories mutually offset by 180°, and magnified portions of same (right-hand) images, illustrating the observation that the portions of the sample closest to the radiation source have better spatial resolution than regions further away from the radiation source.

For moderate cone-angles, a helical trajectory works well. However, as the cone-angle is increased, the resolution in the reconstructed images becomes non-uniform within each reconstructed image. To illustrate this problem, FIG. 5 compares two micro-CT images of the same portion of a carbonate rock specimen from respective tomograms acquired using respective helical trajectories, the only difference being a 180° rotation of the specimen about its cylinder axis between the two helical data acquisition trajectories. The right-hand images are magnified views of a selected region indicated in the respective left-hand images of the sample. It is apparent that the lower one of the magnified images is significantly blurred relative to the upper magnified image. However, if a region near the opposite side of the sample is examined, the converse is observed. The general observation is that the spatial resolution of the image is reduced in regions that correspond to locations within the sample where the distance to the x-ray source was larger during the acquisition of the projection data. Note that, at a voxel resolution of about 4 microns, the spatial resolution is not limited by the source spot-size.

Figure 6:
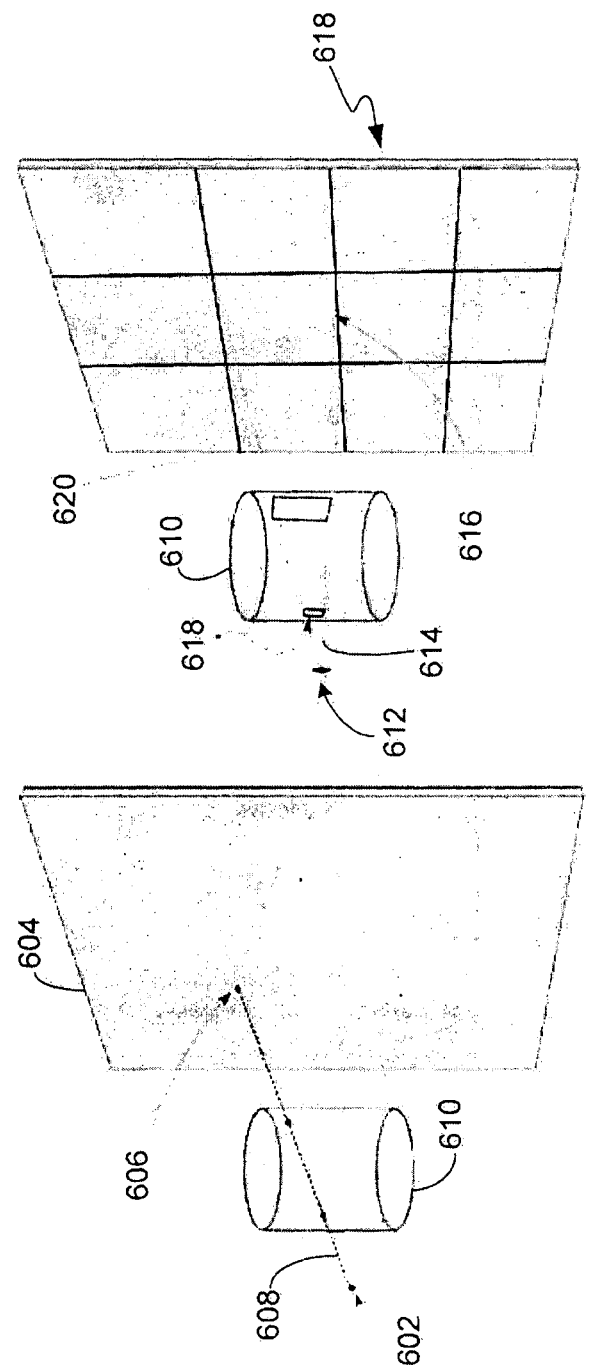
FIG. 6 includes schematic illustrations of the relationship between the dimensions of each detector pixel and the sizes of corresponding regions of a sample on opposite sides of the sample due to the beam divergence in orthogonal directions parallel to the pixel edges.

The cause of this variation in spatial resolution of the reconstruction is that the projection data represents a non-uniform spatial sampling of the object. When deriving filtered backprojection type reconstruction algorithms, the projection data is modelled as the cumulative attenuation of X-rays along lines from a theoretical point source to a continuously sampled detector. In practice, detector sampling is finite. Typically, a detector pixel is much larger than the micro-focus spot size. The real projection data therefore represents not only the cumulative attenuation along the straight lines, but also a spatial average over the solid angle spanned by each detector pixel. Since this solid angle spans a progressively larger geometric area with increasing distance from the (nominally point) source, the finite sampling of each detector pixel is equivalent to applying a non-uniform blurring of the X-ray attenuation map with distance through the sample before acquiring each projection, as illustrated in FIG. 6. The left-hand part of FIG. 6 shows an idealised CT configuration with an x-ray point source 602, and an x-ray detector 604 whose pixels are no larger than the region 606 illuminated by the zero-divergence x-ray beam 608 after it has passed through the sample 610.

In contrast, the right-hand side of FIG. 6 illustrates a more realistic CT configuration, wherein an x-ray spot source 612 of finite dimensions produces a generally conical x-ray beam 614 that passes through the sample 610 to illuminate discrete detector pixels 616 of a detector 618. Due to the finite beam divergence, the lateral dimensions (i.e., dimensions orthogonal to the direction of propagation) of the diverging beam increase with increasing distance from the source 612. Considering a generally rectangular diverging portion of the beam 614 corresponding to the dimensions of an individual detector pixel 616, the lateral dimensions of a volume or slice 618 of the sample 610 close to the x-ray source 612 are therefore smaller than the corresponding lateral dimensions of a second volume 620 of the sample 610 further away from the x-ray source 612. The result of the expanding lateral dimensions of the pixel-sampled volumes with increasing distance from the detector 612 means that the highest spatial resolution is obtained from volumes or slices 618 of the sample closest to the x-ray source 612, and the lowest spatial resolution is obtained from volume 620 furthest away from the x-ray source 612.

Due to the inherent asymmetry of the helix trajectory, the non-uniform sampling persists even when the whole dataset is taken into account: some points will be further away from the source than others, even when averaged over all relevant projections. The degree to which this is the case depends on the pitch of the helix and on the subset of projections that contributes to the reconstruction at each point. Reconstruction using the Katsevich 1PI inversion method represents an extreme case. Since this reconstruction method requires only data from projections that span half a revolution of the helix, it allows the use of very high pitch trajectories, and consequently very rapid scanning of long objects.

Figure 7:
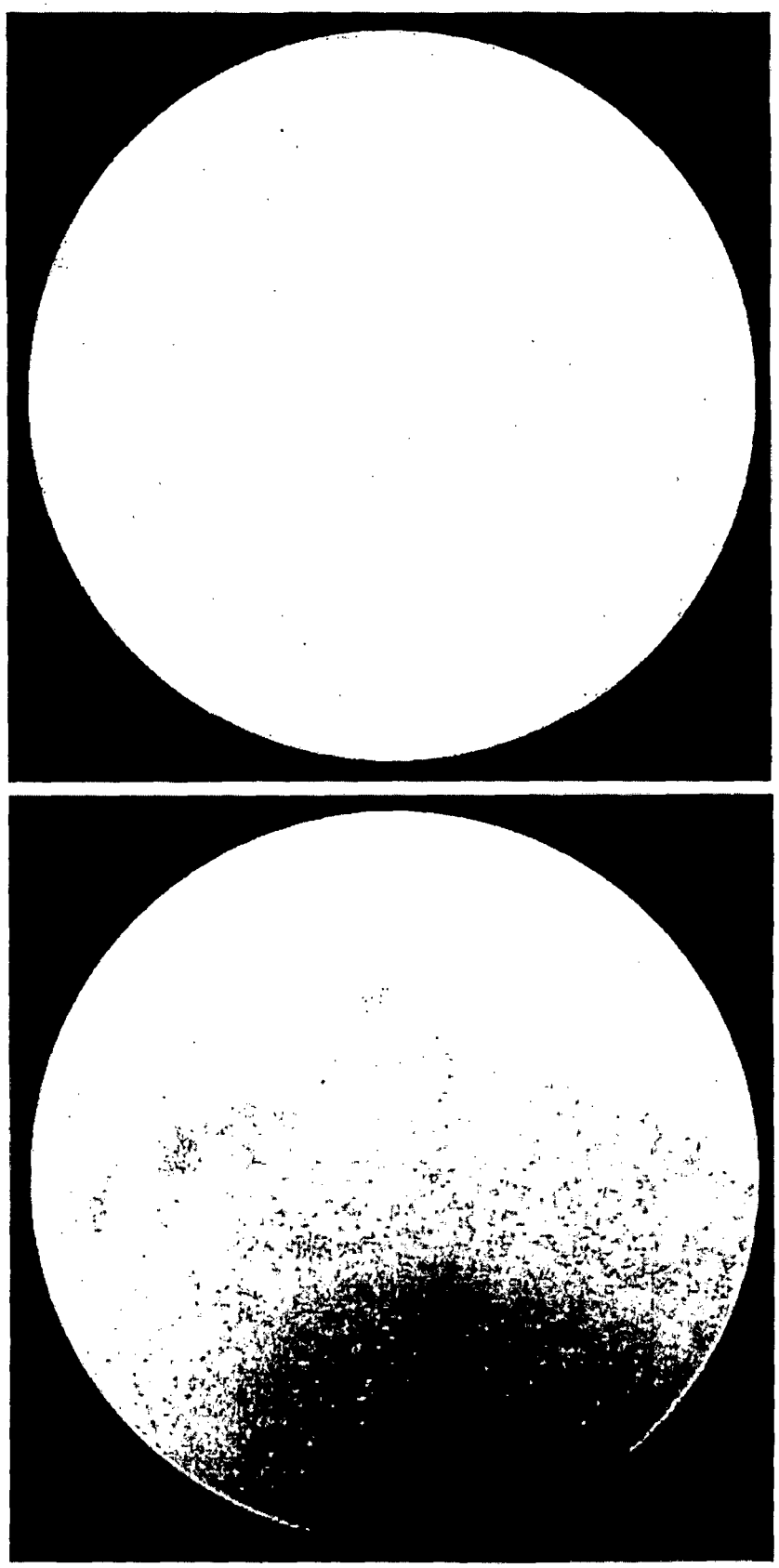
FIG. 7 includes images representing the variation in average source distance for regions of a cylindrical sample in a reconstructed tomogram slice for a single helical complete trajectory (left-hand image) and for the average of two helical complete trajectories mutually offset by 180°.

The left-hand image in FIG. 7 represents (as intensity or brightness) the average distance from the radiation source to each point in a plane inside the reconstructed volume, averaged over all projections that influence the reconstruction at that point. The image clearly demonstrates that the distance from the source to each point inside the reconstructed volume, when averaged over all projections that influence the reconstruction, is spatially variant. This means that the corresponding blurring caused by the finite detector elements and the beam divergence through the sample will also vary spatially.

All prior art exact reconstruction methods have been developed without regard for finite detector elements. Consequently, they do not account for the spatially varying sampling of the object inherent in a projection dataset acquired along a helical trajectory using a divergent beam of radiation. The processes described herein address this oversight, and produce uniform or at least more uniform spatial resolution across the tomogram. This ultimately renders high-resolution 3D imaging more accessible to end users from industry and academic institutions, and provides a better tool for viewing specimen structure with a high degree of clarity and detail.

It is evident from FIG. 7 that regions closer to the radiation source will be reconstructed from projection data with a much lesser degree of blurring induced by the sampling. By reconstructing on a grid which has a constant voxel size, corresponding to the magnification at the rotation axis, prior art reconstruction methods use too small a voxel-size for the regions which on average are far away from the source (regions appear blurry), and conversely too large a voxel-size for the regions that are close to the source on average (regions that appear sharp).

In order to obtain high-quality tomograms with uniform resolution, the reconstruction processes described herein use redundant data in order to compensate for the beam divergence and the varying source distance through the sample.

Given the utility of helical trajectories, the described embodiments use two mutually offset (by 180°) helical trajectories. However, it will be apparent to those skilled in the art that more than two trajectories could be used (e.g., n helical trajectories mutually offset by a rotation angle of 360°/n), and that a wide variety of other possible trajectories could be used in other embodiments, including other forms of complete trajectory such as those described above. Indeed, it is not even necessary that the trajectories be of the same form, although in practice it is convenient for them to be so.

The right-hand image in FIG. 7 is the same as the left-hand image, but where the source distances are effectively averaged by generating the image from two tomograms separately reconstructed from data acquired along the respective helical trajectories. Clearly, this process provides a much more uniform source distance distribution than a single-helix tomogram (left-hand image). The projection dataset therefore contains information representing a more even spatial sampling of the object. As a consequence, it is possible to process this dataset to generate a tomogram having a more uniform spatial resolution.

It will be apparent to those skilled in the art that the projection images acquired using multiple complete trajectories can be combined in a variety of ways. Most simply and conveniently, in some embodiments separate tomograms are reconstructed from the respective image sets for the respective trajectories, and the resulting tomograms combined. However, in an alternative, albeit less convenient, embodiment, the projection images are processed directly to generate a 'corrected' tomogram without needing to generate the intermediate tomograms.

Figure 8:
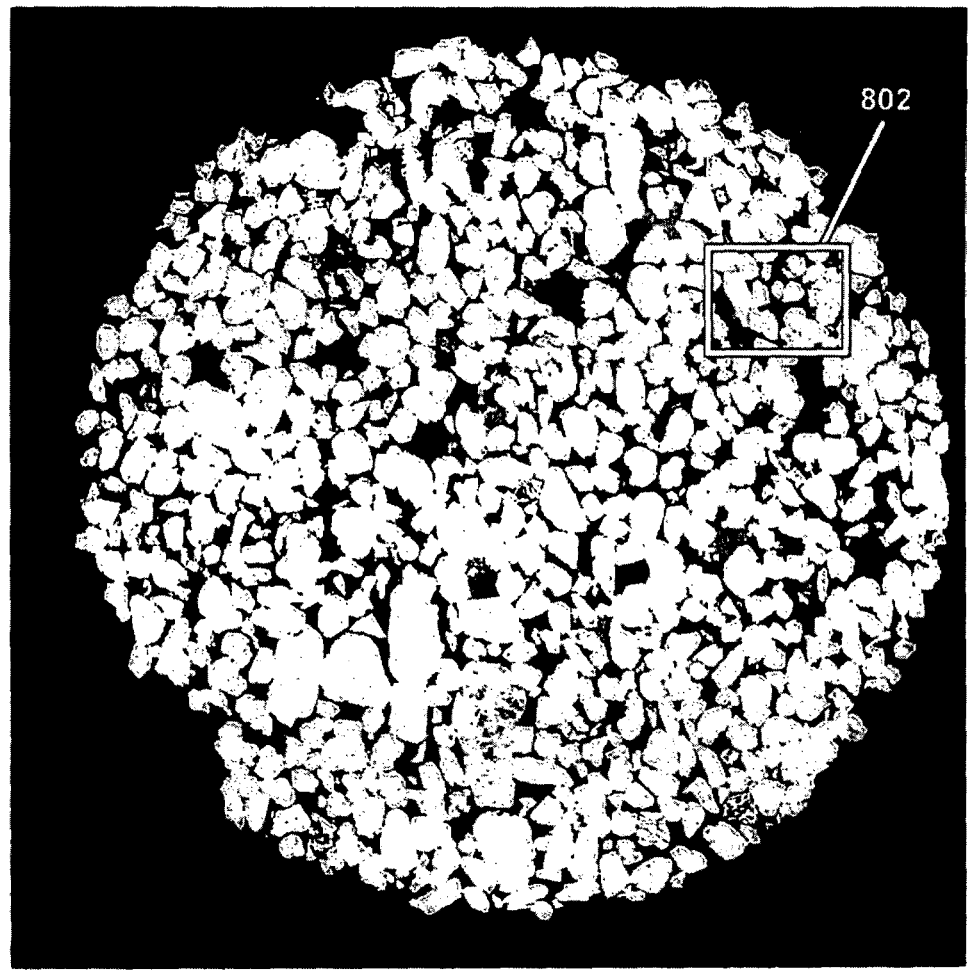
FIG. 8 is an image of a tomogram slice indicating a selected rectangular region that is shown at a higher magnification in FIG. 9.
Figure 9:
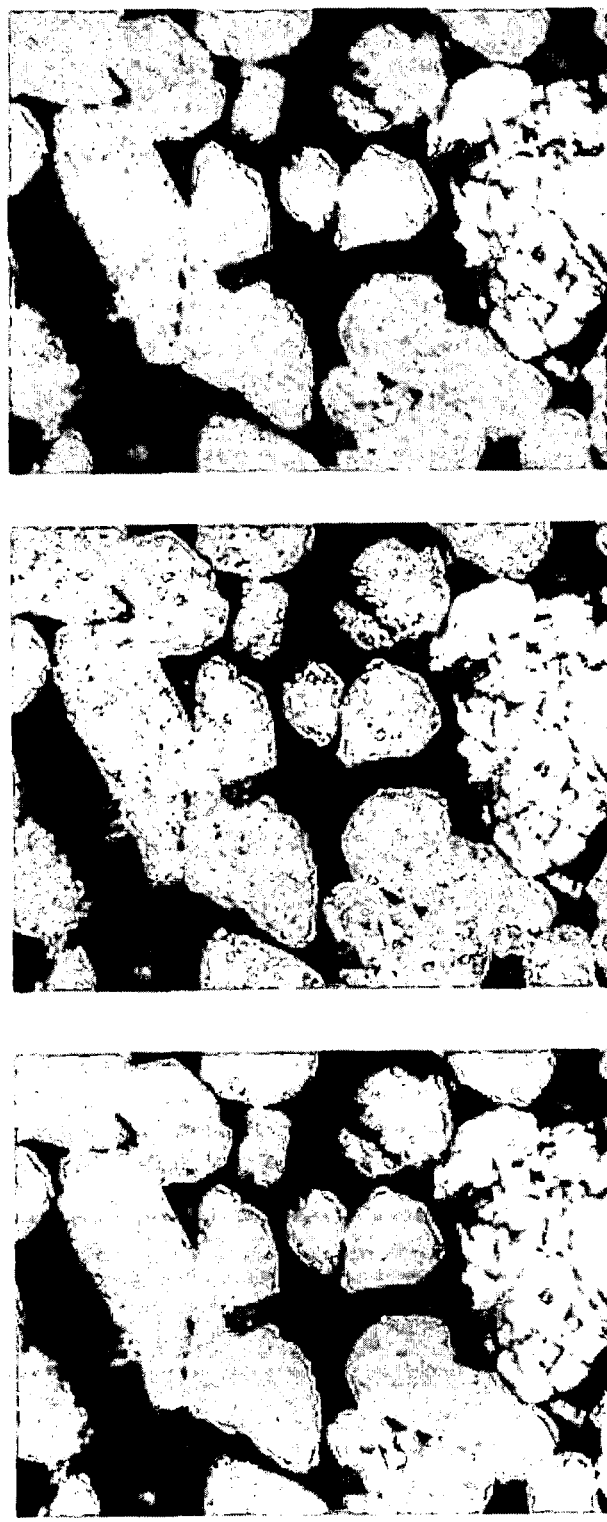
FIG. 9 includes three magnified portions of respective tomograms, corresponding to the selected region indicated in FIG. 8; the top and middle images are from tomograms generated from projections acquired along single helical trajectories mutually offset by 180 degrees, and the lower image is from a tomogram generated from equal-weighted contributions from the projection images for both of the helical trajectories used to generate the top and middle images.

In some embodiments, a single tomogram is generated as a weighted average of the individual tomograms. The most straight-forward weighting scheme is to assign equal weight to each tomogram. FIG. 8 shows a reconstructed image of a tomogram slice, with an overlaid rectangular selection 802 indicating a selected region of the sample that is shown magnified in FIG. 9. The three images in FIG. 9 shows this same region, but from three different tomograms. The top and middle images are from respective tomograms generated from respective sets of projection images, the sets being acquired along respective single helical trajectories mutually offset by, 180 degrees. Close comparison of these two images indicates that the spatial resolution in the selected region of the sample is substantially better in the top image than in the middle image, where the diverging radiation beam has, on average, travelled further from the x-ray source to reach the selected region of the sample than for the top image.

The lower image is from a tomogram generated from equal-weighted contributions from the tomograms for both of the helical trajectories used to generate the top and middle images. Clearly, the spatial resolution in this image is intermediate to that of the upper two images, as expected, albeit with the advantage that the spatial resolution of images generated in this manner is substantially independent of location within the tomogram. To further improve the image sharpness, a non-uniform weighting scheme is used in some embodiments to combine the tomograms in order to selectively or predominantly include only the sharpest region(s) from each tomogram (possibly with a relatively small weighted overlap between regions), and thereby provide substantially the best available spatial resolution at all regions within the final tomogram. These two options represent extremes between which a continuum of possible weighting schemes exists that, for each point in the final reconstruction, will reduce the impact of projection data that represent a sparse spatial sampling, thereby substantially improving the uniformity of the spatial resolution of the final tomogram.

In addition to providing a more uniform reconstruction result, micro-CT imaging using multiple trajectories lends itself to the autofocus alignment process described in International Patent Application No. PCT/AU2011/000038. For example, since the dataset for two 180° offset helical trajectories includes paired projections taken from opposite sides of the object 210, any geometric hardware misalignment will therefore result in a mismatch of the back-projected result, and consequently be detected as a blurred image.

A particular advantage of the multiple trajectory processes described herein is that they provide increased spatial resolution without increasing the acquisition time. In practice, the acquisition time for a given micro-CT imaging apparatus and configuration (whether using single or multiple trajectories) is chosen so that the signal-to-noise ratio of the resulting tomogram is sufficient for its required purpose. However, if multiple trajectories are used, each individual projection image can have more noise than if only one trajectory is used, and yet provide the same noise in the final tomogram. For example, if a weighting scheme which places equal emphasis on two complementary trajectories is employed, the acquisition time per image required when using both trajectories is half that required when using only a single trajectory. Thus the total acquisition time can be substantially independent of the number of trajectories, and yet the spatial resolution is substantially improved when multiple trajectories are used to acquire the projection images.

Figure 10:
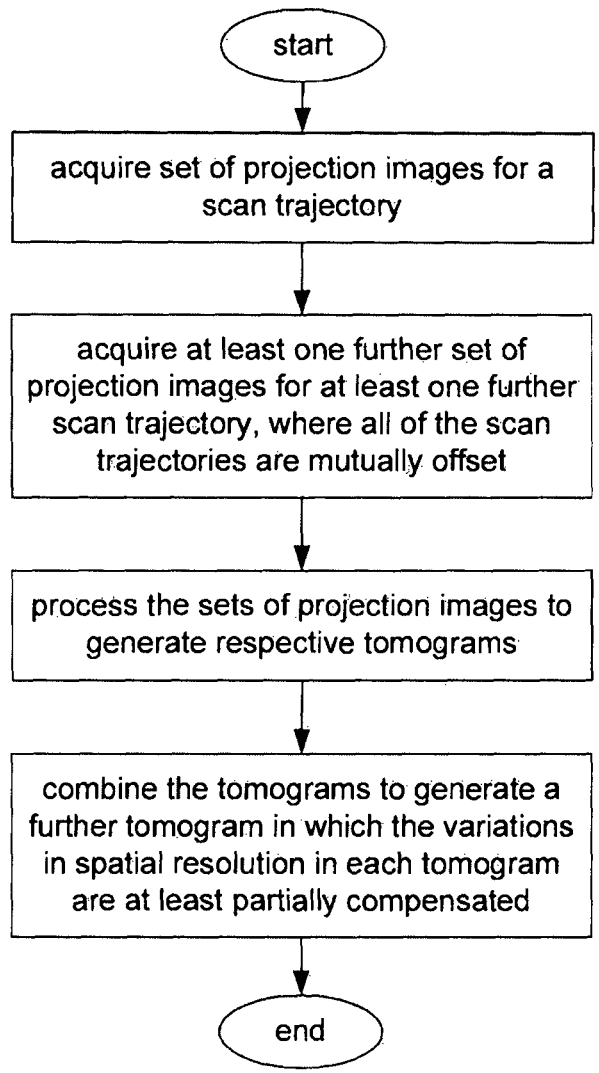
FIG. 10 is a flow diagram of an embodiment of a tomographic imaging process.
Figure 11:
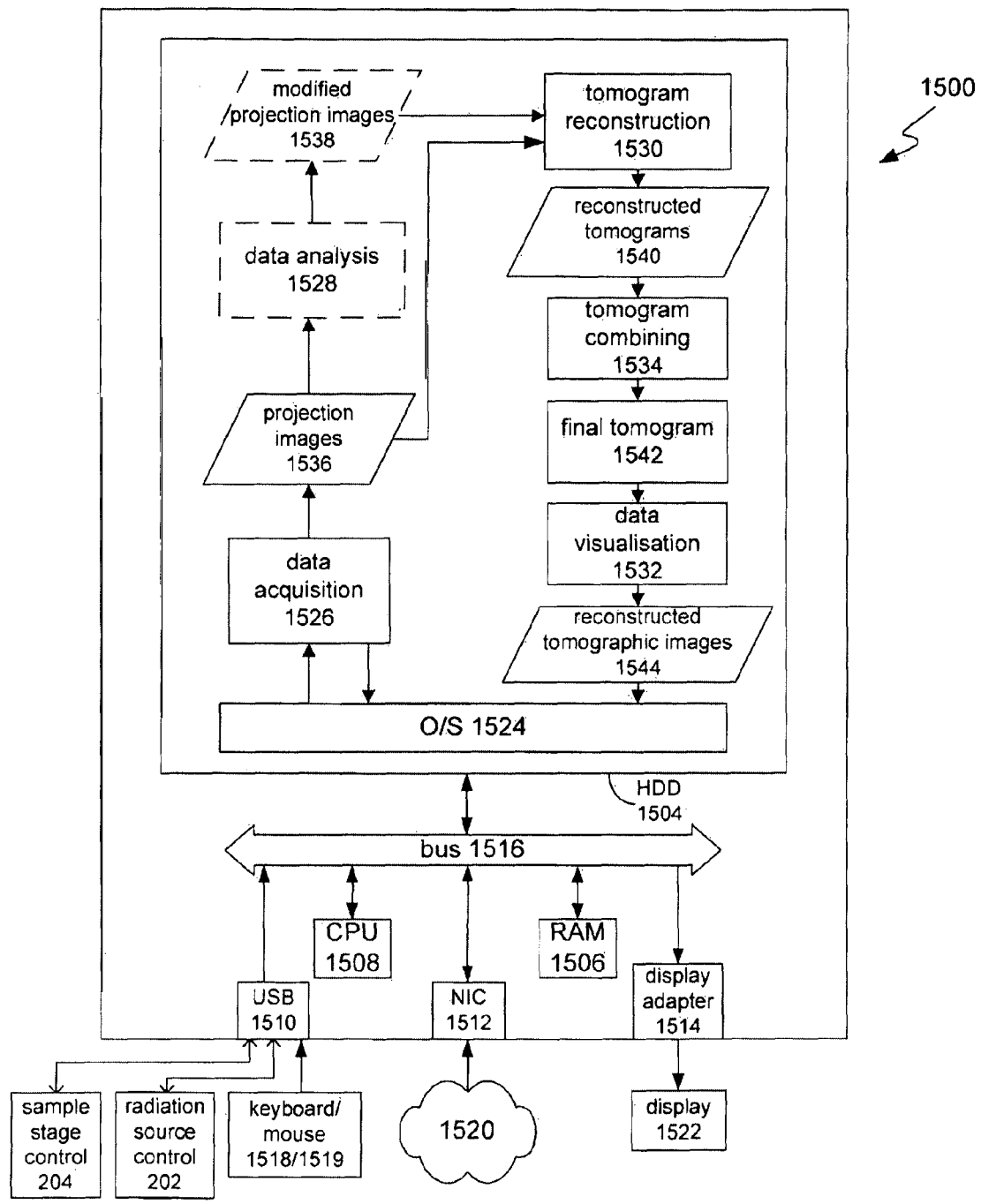
FIG. 11 is a block diagram of a computer system of a computed tomography imaging system.

As will be appreciated by those skilled in the art, the tomographic imaging processes described herein and shown in FIG. 10 can be embodied in a variety of different forms, but may be most conveniently embodied in the form of computer-executable programming instructions of one or more software modules. Accordingly, in the described embodiments, the tomographic imaging apparatus includes a standard computer system 1500 such as an Intel IA-32 or IA-64 based computer system, as shown in FIG. 11, and the tomographic imaging process is executed by the computer system 1500 and is implemented as programming instructions of one or more software modules 1526 to 1534 stored on non-volatile (e.g., hard disk or solid-state drive) storage 1504 associated with the computer system 1500. However, it will be apparent that at least parts of the tomographic imaging process could alternatively be implemented as one or more dedicated hardware components, such as application-specific integrated circuits (ASICs) and/or field programmable gate arrays (FPGAs), for example.

The computer system 1500 includes standard computer components, including random access memory (RAM) 1506, at least one processor 1508, and external interfaces 1510, 1512, 1514, all interconnected by a bus 1516. The external interfaces include universal serial bus (USB) interfaces 1510, at least one of which is connected to a keyboard 1518 and a pointing, device such as a mouse 1519, a network interface connector (NIC) 1512 which connects the system 1500 to a communications network such as the Internet 1520, and a display adapter 1514, which is connected to a display device such as an LCD panel display 1522 for viewing the tomographic images.

The system 1500 also includes a number of other software modules 1524 to 1534, including an operating system 1524 such as Linux, Apple Inc.'s OS X, or Microsoft Windows, a data acquisition module 1526, a tomogram reconstruction module 1530, a tomogram combining module 1534, a data visualisation module 1532, and optionally, a data analysis module 1528. The data acquisition module 1526 controls the sample rotation and translation stage 204, receives data from the detector 206, and stores the received data as sets of projection images 1536 for respective mutually offset complete trajectories. Optionally, a data analysis module 1528 performs an alignment process as described in described in International Patent Application No. PCT/AU2011/000038 to determine values for misalignment parameters of the imaging components 202, 204, 206 of the system, and thereby to generate corresponding sets of corrected projection images 1538. In either case, the projection images 1536 or 1538 are processed by a reconstruction module 1530 to generate reconstructed tomograms 1540 for respective complete trajectories. Finally, a tomogram combining module 1534 combines the tomograms 1540 to provide a final tomogram 1542 from selected portions of the individual tomograms 1540 to provide the best available spatial resolution for each region of the tomograms 1540 (or alternatively at least more uniform spatial resolution). A data visualisation module 1532 can then process the final tomogram 1542 to generate reconstructed tomographic images 1544 in real-time under user control.

It will be apparent to those skilled in the art that the processes executed by the computer system can include control of the radiation source 202 and the CT scanning apparatus that causes the beam of radiation to follow the desired trajectories along the sample or object of interest, and/or the processing of the resulting projection images to generate the final tomogram in which the variations in source distance are at least partially compensated.

Typically, both of these functions will be performed under control of the computer system 1500, but it will be apparent that this need not be the case in some embodiments. For example, there may be one computer system that controls the trajectory of the object and data acquisition, and another, essentially independent computer system that processes the projection images to generate the final tomogram 1538. Moreover, the process can include generating a corresponding tomogram 1542 for each complete trajectory, and then processing or combining the resulting tomograms 1540 to generate the final tomogram 1542 in which the variations in source distance are at least partially compensated to improve the uniformity of spatial resolution within the tomogram. The processing of the individual tomograms 1540 to generate the final tomogram 1542 may be performed independently of the other steps and on an independent computer system.

Many modifications will be apparent to those skilled in the art without departing from the scope of the present invention.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

The invention claimed is:

1. A computed tomography imaging process, including:
   acquiring projection images of an object by detecting radiation that has passed through the object for respective different relative orientations of the object and the radiation; and
   processing the projection images to generate a tomogram of the object;
   wherein the radiation passes through the object in the form of a diverging beam, and the different relative orientations of the object and the beam of radiation define two or more complete trajectories of the beam along the object, the complete trajectories being mutually offset to reduce the degradation of spatial resolution in portions of the generated tomogram due to the divergence of the beam through the object.

2. The process of claim 1, wherein the processing reduces the variation in spatial resolution in the tomogram.

3. The process of claim 2, wherein the different relative orientations of the object and the beam of radiation define a single trajectory that includes the two or more complete trajectories.

4. The process of claim 3, wherein the two or more complete trajectories are acquired independently.

5. The process of claim 3, wherein the two or more complete trajectories are helical trajectories.

6. The process of claim 5, wherein the two or more complete trajectories include mutually offset helical trajectories.

7. The process of claim 5, wherein the two or more complete trajectories include two helical complete trajectories mutually offset by about 180°.

8. The process of claim 7, wherein the processing of the projection images includes:
   processing the projection images for each of the two or more complete trajectories to generate a corresponding first tomogram, wherein the spatial resolution of each said first tomogram varies with spatial location within the object in accordance with the corresponding complete trajectory; and
   processing the first tomograms to generate a further tomogram in which the variation in spatial resolution is reduced or at least partially compensated.

9. The process of claim 8, wherein the further tomogram is generated by combining selected portions of the first tomograms.

10. The process of claim 8, wherein the further tomogram is generated as a weighted combination of the first tomograms.

11. The process of claim 10, wherein the weights are equal.

12. The process of claim 10, wherein the weights are determined so that each portion of the further tomogram substantially corresponds to the sharpest of the corresponding portions of the first tomograms.

13. At least one computer-readable storage medium having stored thereon computer-executable programming instructions configured for execution of the process of claim 1.

14. A computer-readable storage medium having stored thereon a computer program product configured for execution of the process of claim 1.

15. A computed tomography imaging system configured to execute the process of claim 1.

16. A computed tomography imaging process, including:
   accessing sets of projection images of an object or tomograms generated from the sets of projection images of an object, each said set of projection images having been acquired using a corresponding complete trajectory of a beam of radiation relative to the object, wherein the beam divergence through the object degrades the spatial resolution in parts of the corresponding tomogram or in parts of a tomogram generated from the corresponding set of projection images, were such a tomogram to be generated, in accordance with the corresponding complete trajectory; and
   generating a further tomogram from the tomograms or sets of projection images to reduce the degradation in spatial resolution.

17. A computed tomography imaging process, including:
   accessing sets of projection images of an object acquired using respective different complete trajectories of a beam of radiation relative to the object, wherein the beam divergence through the object would degrade the spatial resolution in portions of respective tomograms generated from the respective sets of projection images, were such tomograms to be generated, in accordance with the respective complete trajectories; and
   processing the sets of projection images to generate a tomogram in which the degradation in spatial resolution is reduced.

18. The process of claim 17, wherein the processing reduces the variation in spatial resolution in the tomogram relative to a tomogram from any one of the sets of projection images.

19. The process of claim 18, wherein the tomogram is generated from the projection images using an exact or approximate filtered backprojection-type method.

20. The process of claim 18, wherein the tomogram is generated from the projection images using an iterative approximate method.

21. A computed tomography imaging system, including:
   a data acquisition module configured to acquire projection images of an object generated by detecting radiation that has passed through the object for respective different relative orientations of the object and the radiation; and
   a tomogram generator configured to process the projection images to generate a tomogram of the object;
   wherein the radiation passes through the object in the form of a diverging beam, and the different relative orientations of the object and the beam of radiation define two or more complete trajectories of the beam along the object, the complete trajectories being mutually offset to reduce the degradation of spatial resolution in portions of the generated tomogram due to the divergence of the beam through the object.

22. The computed tomography imaging system of claim 21, wherein the tomogram generator is configured to process the projection images for each of the complete trajectories to generate a corresponding first tomogram, wherein the spatial resolution of each said first tomogram varies with spatial location within the object in accordance with the corresponding complete trajectory; and to process the first tomograms to generate a further tomogram in which the variation in spatial resolution is reduced or at least partially compensated.

* * * * *